United States Patent
Koshimizu (10) Patent No.: US 6,297,064 B1
(45) Date of Patent: Oct. 2, 2001

(54) END POINT DETECTING METHOD FOR SEMICONDUCTOR PLASMA PROCESSING

(75) Inventor: Chishio Koshimizu, Kitakoma-gun (JP)

(73) Assignees: Tokyo Electron Yamanashi Limited, Nirasaki; Agency of Industrial Science and Technology, Kawaguchi, both of (JP)

(*) Notice: Subject to any disclaimer, the term of this patent is extended or adjusted under 35 U.S.C. 154(b) by 0 days.

(21) Appl. No.: 09/600,175
(22) PCT Filed: Feb. 2, 1999
(86) PCT No.: PCT/JP99/00428
    § 371 Date: Aug. 3, 2000
    § 102(e) Date: Aug. 3, 2000
(87) PCT Pub. No.: WO99/40617
    PCT Pub. Date: Aug. 12, 1999

(30) Foreign Application Priority Data

Feb. 3, 1998 (JP) .................................................. 10-022160

(51) Int. Cl.$^7$ .................................................. H01L 21/00
(52) U.S. Cl. .................................. 438/9; 156/345; 216/60; 438/710
(58) Field of Search .................... 216/59, 60, 79; 438/9, 14, 16, 710, 719, 723; 156/345 MT (56) References Cited

U.S. PATENT DOCUMENTS 5,374,327 * 12/1994 Imahashi et al. .................... 438/9

FOREIGN PATENT DOCUMENTS

| 5-029276 | 2/1993 | (JP) . |
| 5-102086 | 4/1993 | (JP) . |
| 5-102089 | 4/1993 | (JP) . |

* cited by examiner

Primary Examiner—William A. Powell
(74) Attorney, Agent, or Firm—Oblon, Spivak, McClelland, Maier & Neustadt, P.C.

(57) ABSTRACT

When plasma-etching a silicon dioxide film with a CF-based gas, the emission intensities (Ia, Ib) of CF-based radicals and carbon monoxide are observed through spectroscopes (61, 62). First, first and second approximate expressions (Fa(x), Fb(x)) which approximate the characteristic curves of the emission intensities (Ia, Ib) within a specified period are obtained, and the ratio of the standard deviations of the emission intensities (Ia, Ib) to the values of the first and second approximate expressions (Fa(x), Fb(x)) is obtained as a correction coefficient α. When the specified period has elapsed, first and second intermediate expressions (Ia/Fa(x), Ib/Fb(b)) are obtained, and a criterion expression ([Ia/Fa(x)]/{α[Ib/Fb(x)−1]+1}, which expresses the ratio of the first intermediate expression to the second intermediate expression and is weight-corrected with the correction coefficient (α), is obtained. The end point of the etching point is determined on the basis of this criterion expression.

17 Claims, 5 Drawing Sheets

END POINT DETECTING METHOD FOR SEMICONDUCTOR PLASMA PROCESSING

TECHNICAL FIELD

The present invention relates to a method of detecting the end point of a semiconductor plasma process in performing the process for a target object and, more particularly, to an end point detection method in dry etching. The semiconductor plasma process refers to various types of plasma processes performed to form a semiconductor layer, insulating layer, conductive layer, and the like on a target object such as a semiconductor wafer or LCD substrate with a predetermined pattern, so that a semiconductor device or a structure including an interconnection, electrode, and the like to be connected to the semiconductor device is manufactured on the target object.

BACKGROUND ART

In the semiconductor device manufacturing process, dry etching is an indispensable technique to form micropatterns. Dry etching is a method of generating a plasma in vacuum by using a reactive gas, and removing an etching target by using ions, neutral radicals, atoms, molecules, and the like in the plasma. If etching is continued after the etching target is completely removed, the underlying material may be unnecessarily etched, or the etching shape may be changed. Therefore, to obtain a structure as designed, it is very important to detect the end point of the etching process accurately.

Jpn. Pat. Appln. KOKAI Publication No. 5-102086 discloses a prior art of the end point detection method in etching, which was filed by the present inventor. According to this method, the end point of a dry etching process is determined on the basis of the intensity ratio of the emission intensity of an active species to the emission intensity of the reaction product, in the etching gas. More specifically, first, a conversion coefficient, which causes the average gradients of characteristic curves respectively representing the changes over time of the emission intensities of the active species and reaction product to coincide with each other in a predetermined specified period, is obtained. After the specified period elapses, the ratio of the emission intensity of the active species to that of the reaction product is detected while correcting the characteristic curves by using this conversion coefficient, and the end point of the dry etching process is determined on the basis of this ratio.

As described above, according to the method disclosed in Jpn. Pat. Appln. KOKAI Publication No. 5-102086, the two characteristic curves representing the emission intensities of the active species and reaction product after the lapse of the specified period are corrected by using the conversion coefficient that causes the average gradients of the two characteristic curves representing the emission intensities of the active species and reaction product to coincide with each other within the specified period. Since the average gradients of the characteristic curves are expressed by straight lines, i.e., linear functions, it is difficult to ideally overlay the non-linear two characteristic curves after the lapse of a specified period, as shown in FIG. 2 of this reference. Since the average gradients of the characteristic curves largely differ depending on the width of the specified period, the reliability of end point determination largely depends on the width of the specified period.

Furthermore, the method described above aims at correcting the fluctuations in emission intensities of the active species and reaction product, which are caused by a slight variation in output from the power supply, the influence of a mass-flow controller, a variation in process pressure, an increase in temperature of the target object due to the plasma, and the like, by canceling each other. However, the fluctuation components of the emission intensities of two different materials differ regardless of whether they are active species or reaction products. Accordingly, this method cannot sufficiently correct these different fluctuation components.

DISCLOSURE OF INVENTION

The present invention has been made to solve the conventional problems as described above, and has as its object to provide a method which, when a target object such as a semiconductor wafer or LCD substrate is subjected to a semiconductor plasma process, can accurately detect the end point of the process.

According to the first aspect of the present invention, there is provided an end point detection method in a semiconductor plasma process, comprising the steps of:

determining a specified period set before an ideal end point of the plasma process is reached;

subjecting a target object to the plasma process;

obtaining, during the plasma process, an approximate expression which approximates a characteristic curve representing a change over time in emission intensity of a gas in the plasma within the specified period;

obtaining, during the plasma process, a criterion expression representing a ratio or difference between the emission intensity of the gas in the plasma and a value of the approximate expression after the specified period elapses; and determining an end point of the plasma process on the basis of the criterion expression.

According to the second aspect of the present invention, there is provided an end point detection method in a semiconductor plasma process, comprising the steps of:

determining first and second specified periods set before an ideal end point of the plasma process is reached;

subjecting a target object to the plasma process;

obtaining, during the plasma process, a first approximate expression which approximates a characteristic curve representing a change over time in emission intensity of a first gas in the plasma within the first specified period, and a second approximate expression which approximates a characteristic curve representing a change over time in emission intensity of a second gas in the plasma within the second specified period;

obtaining, during the plasma process, first and second intermediate expressions representing ratios or differences between the emission intensities of the first and second gases in the plasma and values of the first and second approximate expressions after the first and second specified periods elapse;

obtaining a criterion expression representing a ratio of the first intermediate expression to the second intermediate expression; and determining an end point of the plasma process on the basis of the criterion expression.

According to the third aspect of the present invention, there is provided an end point detection method in a semiconductor plasma process, comprising the steps of:

determining first to fourth specified periods set before an ideal end point of the plasma process is reached;

subjecting a target object to the plasma process;

obtaining, during the plasma process, a first approximate expression which approximates a characteristic curve representing a change over time in emission intensity of a first gas in the plasma within the first specified period, and a second approximate expression which approximates a characteristic curve representing a change over time in emission intensity of a second gas in the plasma within the second specified period;

obtaining, during the plasma process, a first deviation corresponding to a deviation of the emission intensity of the first gas in the plasma with respect to a value of the first approximate expression within the third specified period, and a second deviation corresponding to a deviation of the emission intensity of the second gas in the plasma with respect to a value of the second approximate expression within the fourth specified period;

obtaining, during the plasma process, first and second intermediate expressions representing ratios or differences between the emission intensities of the first and second gases in the plasma and the values of the first and second approximate expressions after the first to fourth specified periods elapse;

correcting the first and second intermediate expressions with the first and second deviations, and obtaining a criterion expression representing a ratio of the first intermediate expression to the second intermediate expression; and determining an end point of the plasma process on the basis of the criterion expression.

In the method according to either one of the first to third aspects described above, a time point at which an average gradient of a curve expressed by the criterion expression changes largely, or a time point at which an absolute value of a calculation value of the criterion expression becomes not less than a threshold value, can be determined as a reference for determining the end point.

In the method according to the second or third aspect described above, the first and second approximate expressions can be obtained by using different functions. The first and second specified periods can be the same period. One of the first and second gases can be a gas generated by dissociation of a process gas supplied for the plasma process, and the other one can be a product gas generated by the plasma process.

In the method according to the third aspect described above, the criterion expression can be a ratio, weight-corrected with a correction coefficient, of the first intermediate expression to the second intermediate expression, and the correction coefficient can be a ratio of the first deviation to the second deviation. The first and second deviations can be respectively standard deviations. The first and second deviations can be differences between the maximum and minimum values of deviations. The first to fourth specified periods can be the same period.

BEST MODE FOR CARRYING OUT THE INVENTION

A plasma dry etching method to which an end point detection method according to an embodiment of the present invention is applied will be described with reference to the accompanying drawings.

Figure 1:
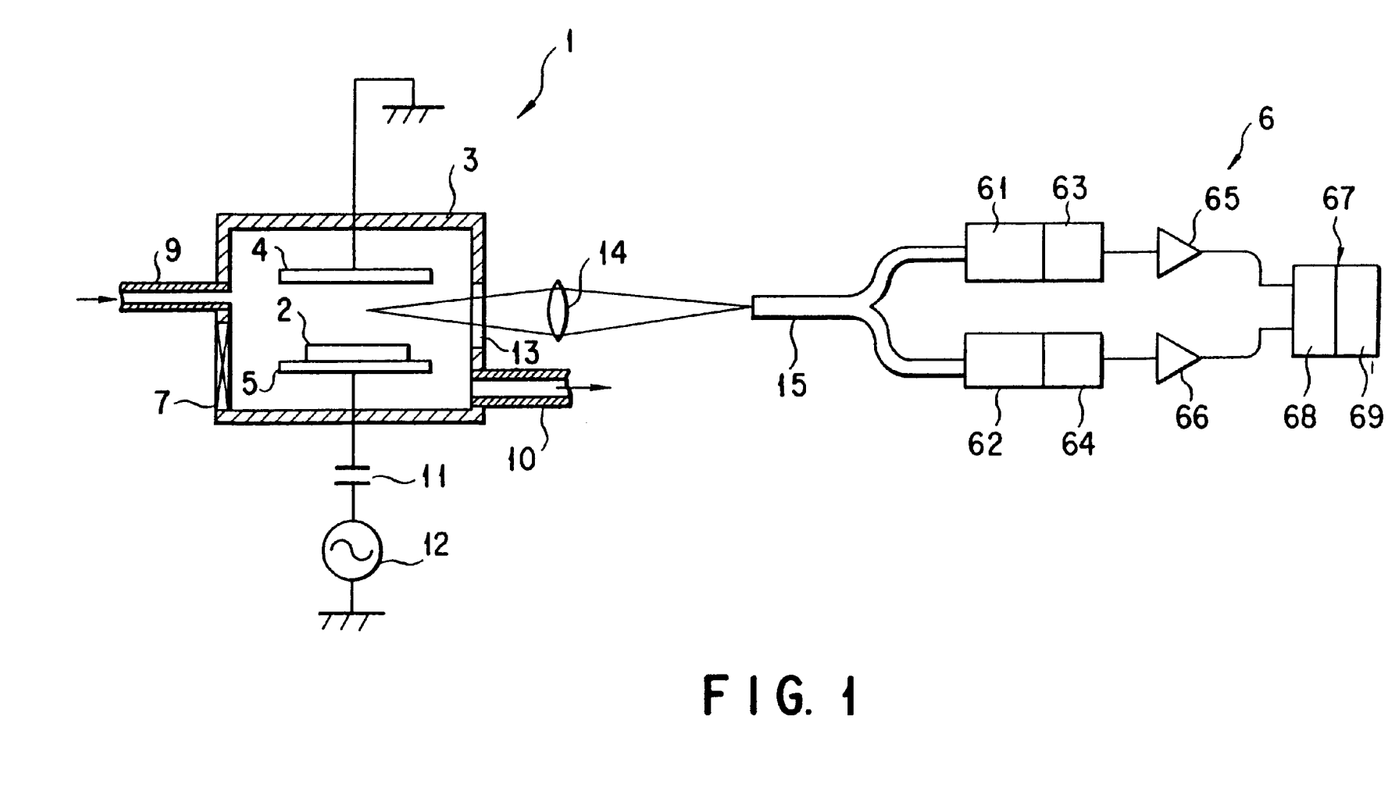
FIG. 1 is a view showing a dry etching apparatus for practicing a method according to the present invention.

FIG. 1 shows a dry etching apparatus 1 for practicing the method according to the present invention. The dry etching apparatus 1 has a vacuum chamber 3 in which a pair of electrodes 4 and 5 oppose each other. A controller 6 is provided to the vacuum chamber 3 to monitor the emission spectrum in the vacuum chamber 3. A process gas such as an etchant is introduced in the vacuum chamber 3 and converted into a plasma, and a target object 2 such as a semiconductor wafer is etched. With the etching process, a silicon dioxide film formed on the target object 2, e.g., a silicon wafer, is selectively etched.

The vacuum chamber 3 is connected to a cassette chamber (not shown) through a gate valve 7 to accommodate the target object 2 through a load-lock chamber (not shown), if necessary. The gate valve 7 is open, and the target object 2 is unloaded and loaded from and into the vacuum chamber 3 with a transfer mechanism (not shown).

The vacuum chamber 3 is connected to a gas inlet pipe 9, through which an etchant such as a CF-based gas, e.g., $CHF_3$ or $CF_4$, and an inert gas such as argon or helium are introduced into the vacuum chamber 3.

The vacuum chamber 3 is also connected to an exhaust pipe 10, through which an excessive gas, a reaction production gas, and the like are exhausted during the etching process, so that the interior of the vacuum chamber 3 is maintained at a predetermined vacuum degree, e.g., about 200 mTorr.

The electrodes 4 and 5 constitute parallel-plate electrodes. One electrode, e.g., the upper electrode 4, is ground, and the other one, lower electrode 5 is connected to an RF power supply 12 through a capacitor 11. The RF power supply 12 can apply an RF voltage across the two electrodes 4 and 5. The lower electrode 5 serves as a worktable for placing the target object 2. A fixing means such as an electrostatic chuck or clamp is provided to the lower electrode 5 to fix the target object 2 reliably.

A window 13 for transmitting light emitted by the plasma generated between the electrodes 4 and 5 is formed in the side surface of the vacuum chamber 3. A lens 14 for focusing light transmitted through the window 13 is set close to the window 13. Light focused by the lens 14 is split by an optical fiber 15 into two beams, and the two beams are sent to the controller 6. In order to detect light emission with a wavelength of up to near 200 nm, the window 13, lens 14, and optical fiber 15 are made of an ultraviolet ray transmissible material such as quartz.

In the controller 6, the two beams of light split by the optical fiber 15 are respectively sent to spectroscopes 61 and 62 so that they are formed into spectra having predetermined ranges. The spectra with specific wavelengths are photoelectrically converted by photoelectric converters 63 and 64, amplified and filtered by amplifiers 65 and 66 each with a low-pass filter, and sent to a determination unit 67. In the determination unit 67, electrical signals corresponding to the beams with the specific wavelengths are subjected to a predetermined arithmetic process, and the end point of the etching process is determined from the result of the arithmetic operation.

One spectroscope 61 and photoelectric converter 63 are used to form a system for the etchant such as $CF_1$ or $CF_2$ radicals. If the etchant is $CF_2$ radicals, this system monitors light with a wavelength falling within a range of 240 nm to 350 nm, e.g., 255.06 nm, 259.5 nm, 262.8 nm, and 271.1 nm. In the range of 240 nm to 350 nm corresponding to the emission wavelength band of $CF_2$, argon as the additive gas emits light particularly less. As $CF_2$ is an etching gas, its light emission is much stronger than light emission of the reaction product. Therefore, light within this wavelength band can be formed by using an inexpensive interference filter having a comparatively low resolution. In particular, if an interference filter having a transmission central wavelength of 260 nm to 270 nm and a half-width of 10 nm to 20 nm is used, photoelectric conversion can be achieved by inexpensive silicon photodiodes without using highsensitive, expensive photomultipliers.

The other spectroscope 62 and photoelectric converter 64 are used to form a system for the reaction production gas, e.g., carbon monoxide. This system may monitor a wavelength of 482.7 nm, as in the conventional case, and preferably monitors a specific wavelength selected from desired wavelengths within the range of 210 nm to 236 nm, and more particularly, either 219.0 nm, 230.0 nm, 211.2 nm, 232.5 nm, or 224 nm to 229 nm. Since the emission spectrum of argon overlaps that of the etchant $CF_1$ comparatively less and does not overlap emission of the etchant $CF_2$, when light within the range of 210 nm to 236 nm is selected, its change can be monitored accurately even if the opening ratio of the etching target portion is small and the amount of production gas is small.

In order to detect a wavelength falling within this range, as the spectroscopes 61 and 62, ones highly sensitive to light with a wavelength of 300 nm or less are preferably used. The determination unit 67 is constituted by, e.g., an A/D converter 68 and CPU 69, monitors the emission intensities to obtain their changes, and performs arithmetic operation to be described later, to detect the end point of the etching process.

A dry etching method according to the present invention in the dry etching apparatus 1 having the above arrangement will be described.

A semiconductor wafer as the target object 2 is transferred from a load-lock chamber (not shown) by a transfer mechanism (not shown) and placed on the lower electrode 5. A photoresist mask having a predetermined pattern shape is already formed on the silicon dioxide film of the semiconductor wafer 2 by an exposure process.

The gate valve 7 is closed, and the interior of the vacuum chamber 3 is evacuated to a predetermined vacuum degree through the exhaust pipe 10. Successively, CF-based gases serving as etching gases, e.g., $CF_3$ gas and $CF_4$ gas, and an inert gas such as argon gas are introduced into the vacuum chamber 3 through the gas inlet pipe 9 with predetermined flow rates, while continuously evacuating the interior of the vacuum chamber 3 through the exhaust pipe 10, to maintain the interior of the vacuum chamber 3 at a predetermined gas pressure. In this state, RF power with a predetermined frequency, e.g., 13.56 MHz, and a predetermined power value, e.g., several hundred W, is applied across the electrodes 4 and 5 to convert the etching gases and inert gas into a plasma. The silicon dioxide portion on the surface of the target object 2 is etched by using this plasma.

The CF-based gas introduced into the vacuum chamber 3 dissociates in the plasma to generate many types of active species, which take part in the etching chemical function. For example, when $CF_2$ gas is selected as an example of the active species, its $CF_2$ radicals and silicon dioxide react as follows:

$$2CF_2 + SiO_2 \rightarrow SiF_4 + 2CO$$

By this reaction, reaction products such as carbon monoxide, $CO^+$ ions, hydrogen radicals, and fluorine radicals are generated.

Carbon monoxide and $CO^+$ ions as the production gas, argon gas as the plasma stabilizing gas, and CF gas as the etching gas respectively emit light with specific spectra. As the plasma emits all these light beams, the emitted light beams are sent from the window 13 of the vacuum chamber 3 to the controller 6 through the lens 14 and optical fiber 15. The spectroscope 61 and 62 form spectra of the sent light beams, and respectively send the light beams with specific wavelengths to the photoelectric converters 63 and 64.

Each emission spectrum input to the spectroscope 61 or 62 is a synthesis of the emission spectra of a plurality of gases. The emission spectrum of carbon monoxide or $CO^+$ ions almost completely overlaps the spectrum of argon gas which exists in the largest amount in the range of 350 nm to 860 nm. However, within the range of 210 nm to 236 nm, particularly at the wavelengths of 219.0 nm, 230.0 nm, 211.2 nm, 232.5 nm, and 224 nm to 229 nm, emission originated from carbon monoxide or $CO^+$ ions is observed. The $CF_2$ gas as the active species has an emission peak at wavelengths of 255 nm and 259.5 nm, which fall outside the spectrum range of argon gas.

More specifically, the spectroscope 61 is set to, e.g., a wavelength of 255 nm, and the spectroscope 62 is set to a specific wavelength selected from wave-lengths within the range of 210 nm to 236 nm. The photoelectric converters 63 and 64 convert the light beams from the spectroscopes 61 and 62 into electric signals with intensities corresponding to these emission intensities. These changes in emission intensities that accompany a change in active species of the etching gas and in production gas are sent to the determination unit 67 through the amplifiers 65 and 66 as the magnitudes of electrical signals output from the photoelectric converters 63 and 64. On the basis of these electrical signals, the determination unit 67 performs predetermined arithmetic operation to determine the end point of the etching process.

An end point detection method performed by the determination unit 67 will be described in detail.

Prior to the start of the plasma process, i.e., the etching process, the operator determines a specified period set before an ideal end point of the etching process is reached, e.g., a period of 60 sec to 150 sec since the start of the etching process (e.g., since the RF power supply 12 is turned on), and inputs and sets this specified range in the determination unit 67. More specifically, a rough etching rate is measured in advance with the same etching conditions, or the etching rate is calculated on the basis of past data. A rough necessary etching time is calculated from the film thickness data of a wafer which is to be processed actually. A time point at which 10% to 30% of this time has elapsed is determined as the start time point of the specified period, and a time point at which 50% to 90% has elapsed is determined as the end time point of the specified period.

The operator also obtains the first and second canonical expressions for obtaining first and second approximate expressions Fa(x) and Fb(x), which respectively approximate characteristic curves representing changes over time in emission intensities of two gases employed as the observation targets, and inputs and sets them in the determination unit 67. For example, in this embodiment, as the two gases employed as the observation targets are CF-based radicals and carbon monoxide, the following exponential function, i.e., $$y=y0+G \cdot e(-(x-x0)/T)$$

can be commonly used as the first and second canonical expressions. Note that y is an emission intensity, y0 is an offset of y, x is a process time, x0 is an offset of x, G is an amplification coefficient, and T is an attenuation constant. Note that y0, x0, G, and T are constants determined when obtaining the approximate expressions. As the first and second canonical expressions, those that are optimum for obtaining the first and second approximate expressions must be selected. Accordingly, depending on the two gases as the observation targets, different canonical expressions are naturally used.

Based on these preset conditions, the determination unit 67 performs the following arithmetic process during the etching process, to determine the end point of the etching process.

First, the first and second approximate expressions Fa(x) and Fb(x) respectively approximating the characteristic curves representing the changes over time in emission intensities Ia and Ib of the CF-based radicals and carbon monoxide in the plasma obtained with two spectrum systems within the specified period (60 sec to 150 sec), are obtained. For example, the first and second approximate expressions can be led by approximating the respective characteristic curves with the known method of least squares on the basis of the canonical expressions described above.

A ratio (Da/Db) between first and second deviations Da and Db respectively expressing the deviations of the emission intensities Ia and Ib of the CF-based radicals and carbon monoxide with respect to the values of the first and second approximate expressions Fa(x) and Fb(x) within the specified period (60 sec to 150 sec), is obtained as a correction coefficient α. As the first and second deviations Da and Db, for example, standard deviations or differences between the maximum and minimum values of deviations can be used.

The specified periods for obtaining the first and second approximate expressions Fa(x) and Fb(b), i.e., the specified periods when the characteristic curves representing the changes over time in emission intensities of the two gases as the observation targets are to be respectively approximated, can be set independently. Also, the specified periods for obtaining the first and second deviations Da and Db, i.e., the specified periods when the respective deviations of the emission intensities Ia and Ib of the two gases as the observation targets are to be obtained, can be set independently. Furthermore, the specified periods for obtaining the first and second approximate expressions Fa(x) and Fb(x), and the specified periods for obtaining the first and second deviations Da and Db, can be set independently of each other.

When the specified period has elapsed (after 150 sec has elapsed), first and second intermediate expressions, e.g., Ia/Fa(x) and Ib/Fb(x), representing the ratios of the emission intensities Ia and Ib of the CF-based radicals and carbon monoxide in the plasma to the values of the first and second approximate expressions Fa(x) and Fb(x), are obtained. Also, a criterion expression given by, e.g., $$[Ia/Fa(x)]/\{\alpha[Ib/Fb(x)-1]+1\} \qquad \{1\}$$

which represents the ratio of the value of the first intermediate expression Ia/Fa(x) to that of the second intermediate expression Ib/Fb(x) and is weight-corrected with the correction coefficient α so that the difference between the first and second deviations Da and Db becomes small, is obtained.

On the basis of this criterion expression, the end point of the etching process is determined, and the determination unit 67 outputs an end signal for ending the etching process. More specifically, the end signal from the determination unit 67 controls the dry etching apparatus 1 to stop supply of the process gas, application of the RF power, and the like, thereby ending the etching process. The end point of the etching process can be determined with reference to, e.g., a time point at which the average gradient of a curve expressed by the criterion expression changes largely. Alternatively, the end point of the etching process can be determined with reference to a time point at which the absolute vale of the calculation value of the criterion expression becomes equal to the threshold value or more. In either case, a time point at which a predetermined time for overetching, which is obtained through experiences, has elapsed from the reference time point can be determined as the end point of the etching process.

The first and second intermediate expressions obtained after the lapse of the specified period (after 150 sec elapses) can be expressions, e.g., Ia−Fa(x) and Ib−Fb(x), representing the differences between the emission intensities Ia and Ib of the CF-based radicals and carbon monoxide in the plasma and the values of the first and second approximate expressions Fa(x) and Fb(x). In this case, a criterion expression given by, e.g., $$[Ia-Fa(x)+M]/\{\alpha[Ib-Fb(x)]+M\} \qquad \{2\}$$

representing the ratio between the values of the first and second intermediate expressions Ia−Fa(x) and Ib−Fb(x), which is weight-corrected with the correction coefficient α so that the difference between the first and second deviations Da and Db becomes small, is obtained. Note that M is an arbitrary constant, e.g., 1. On the basis of this criterion expression, the end point of the etching process is determined, and the dry etching apparatus 1 is controlled to end the etching process.

[Embodiments]

A silicon wafer having a silicon dioxide film covered with a photoresist mask having an opening ratio of 1% was employed as the target object 2, and plasma etching process and detection of the emission intensity of the plasma were performed by the etching apparatus 1 shown in FIG. 1 under the above conditions. More specifically, $CHF_3$ and $CF_4$ were introduced as the etching gases into the vacuum chamber both at 60 SCCM, and argon gas was introduced into the vacuum chamber at 800 SCCM. The interior of the vacuum chamber was set at 750 mTorr, RF 13.56 MHz, and 600 W, and the wafer temperature was set to −25° C. During the etching process, the emission intensity of a spectrum of 255 nm or 271 nm was determined as the emission intensity of the CF-based radicals, and the emission intensity of a spectrum of 219 nm was determined as the emission strength of carbon monoxide. The specified period was set to 60 sec to 150 sec from the start of the etching process. As the first and second canonical expressions for obtaining the first and second approximate expressions Fa(x) and Fb(x), y=y0+G·e(−(x−x0)/T) described above was used.

Figure 2:
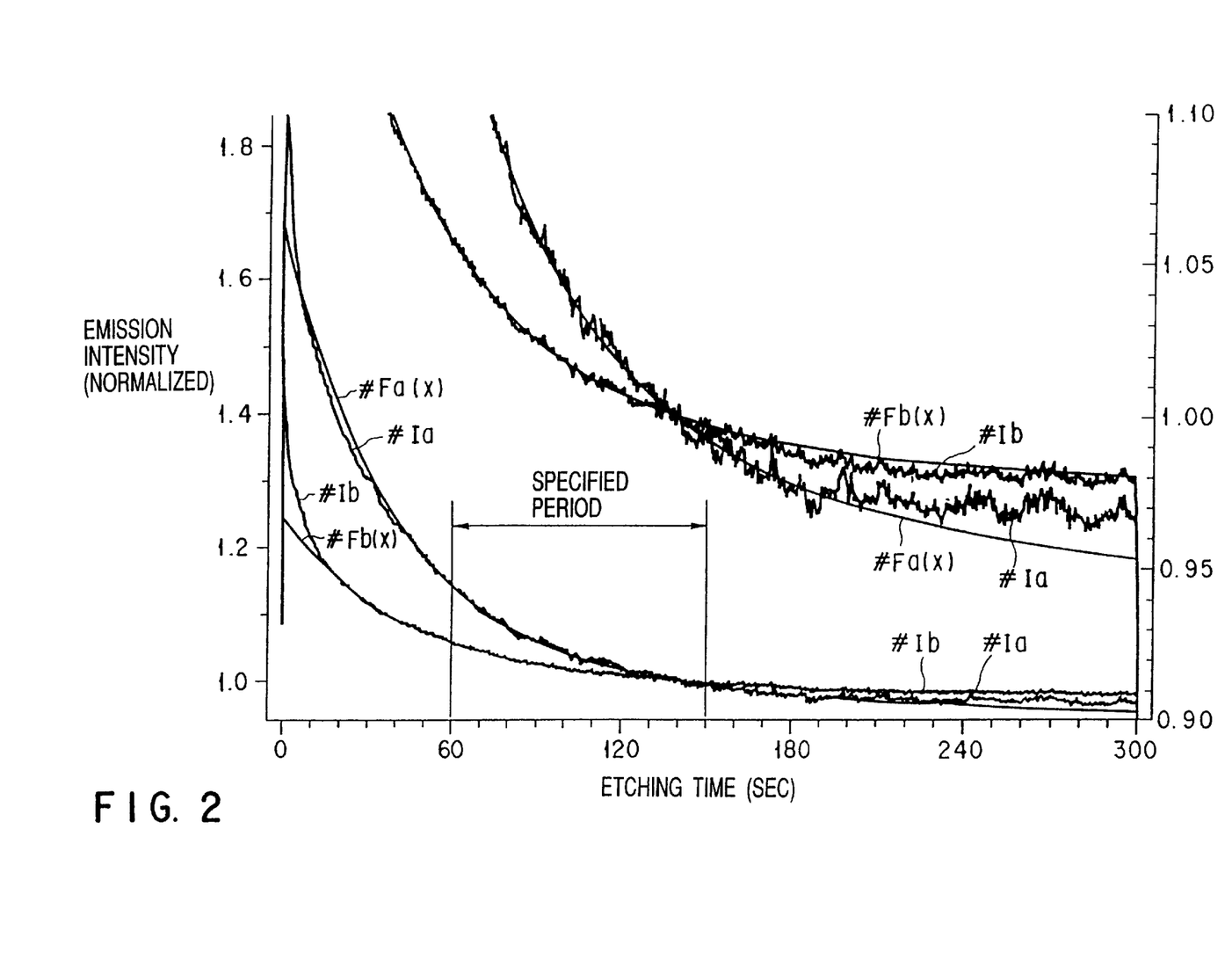
FIG. 2 is a graph showing changes over time in emission intensities obtained in an experiment according to an embodiment of the present invention, and approximate curves representing these changes over time.

FIG. 2 shows changes over time in emission intensities obtained in this experiment, and their approximate curves. In FIG. 2, the emission intensities are normalized with reference to the values obtained upon a lapse of 140 sec from the start of the etching process, as 1.0. #Ia and #Ib denote characteristic curves representing the changes over time in emission intensities Ia and Ib of the CF-based radicals and carbon monoxide, respectively, throughout the entire period of the etching process. #Fa(x) and #Fb(x) denote approximate curves calculated in accordance with the first and second approximate expressions Fa(x) and Fb(x), which respectively approximate the characteristic curves of the emission intensities within the specified period (60 sec to 150 sec), throughout the entire period of the etching process. In FIG. 2, the curves #Ia, #Ib, #Fa(x), and #Fb(x) on the lower side are plotted along the scale of the left axis of ordinate, and the curves #Ia, #Ib, #Fa(x) and #Fb(x) on the upper side are plotted in an enlarged scale corresponding to the scale of the right axis of ordinate.

A ratio (Da/Db) between the first and second deviations Da and Db, respectively expressing the deviations of the emission intensities Ia and Ib of the CF-based radicals and carbon monoxide with respect to the values of the first and second approximate expressions Fa(x) and Fb(x) within the specified period (60 sec to 150 sec), was obtained as a correction coefficient α. When standard deviations were used as the first and second deviations Da and Db, Da/Db= 2.48. When differences between the maximum and minimum values of deviations were used as the first and second deviations, Da/Db=α=2.5.

Figure 3:
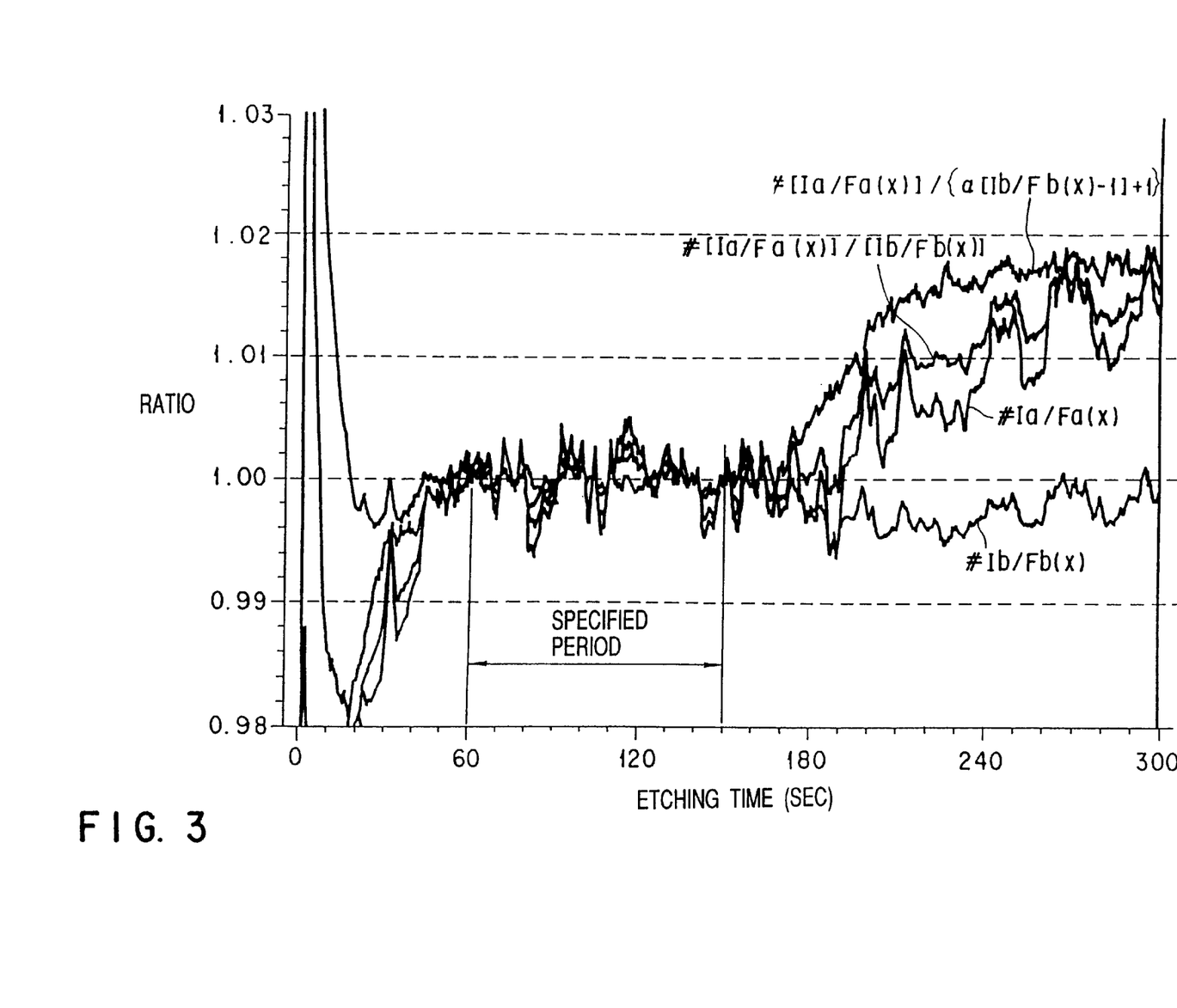
FIG. 3 is a graph showing curves expressed by intermediate expressions, a criterion expression, and the like obtained from data shown in FIG. 2 by arithmetic operation.

FIG. 3 shows curves expressed by the intermediate expressions, the criterion expression, and the like obtained by the arithmetic operation of the determination unit 67. Referring to FIG. 3, #Ia/Fa(x) and #Ib/Fb(x) respectively denote the curves of the first and second intermediate expressions Ia/Fa(x) and Ib/Fb(x). #[Ia/Fa(x)]/{α[Ib/Fb(x)−1]+1} and #[Ia/Fa(x)]/[Ib/Fb(x)] denote the curves of the criterion expression {1} described above and of expression of its comparative example given by:

[Ia/Fa(x)]/[Ib/Fb(x)]  {3}

As the correction coefficient α, 2.48 based on the standard deviation is used.

As shown in FIG. 3, in the curve of criterion expression {1}, the fluctuation of the curve was much smaller than that of the curve of expression {3} of the comparative example, and a large change with an average gradient was obtained near 200 sec, which is close to the end point of the etching process. From comparison of expressions {1} and {3}, these changes are obviously brought about by the weighting correction using the correction coefficient α. More specifically, with the weight-corrected criterion expression according to the present invention, the end point of the etching process could be detected more easily and accurately.

Figure 4:
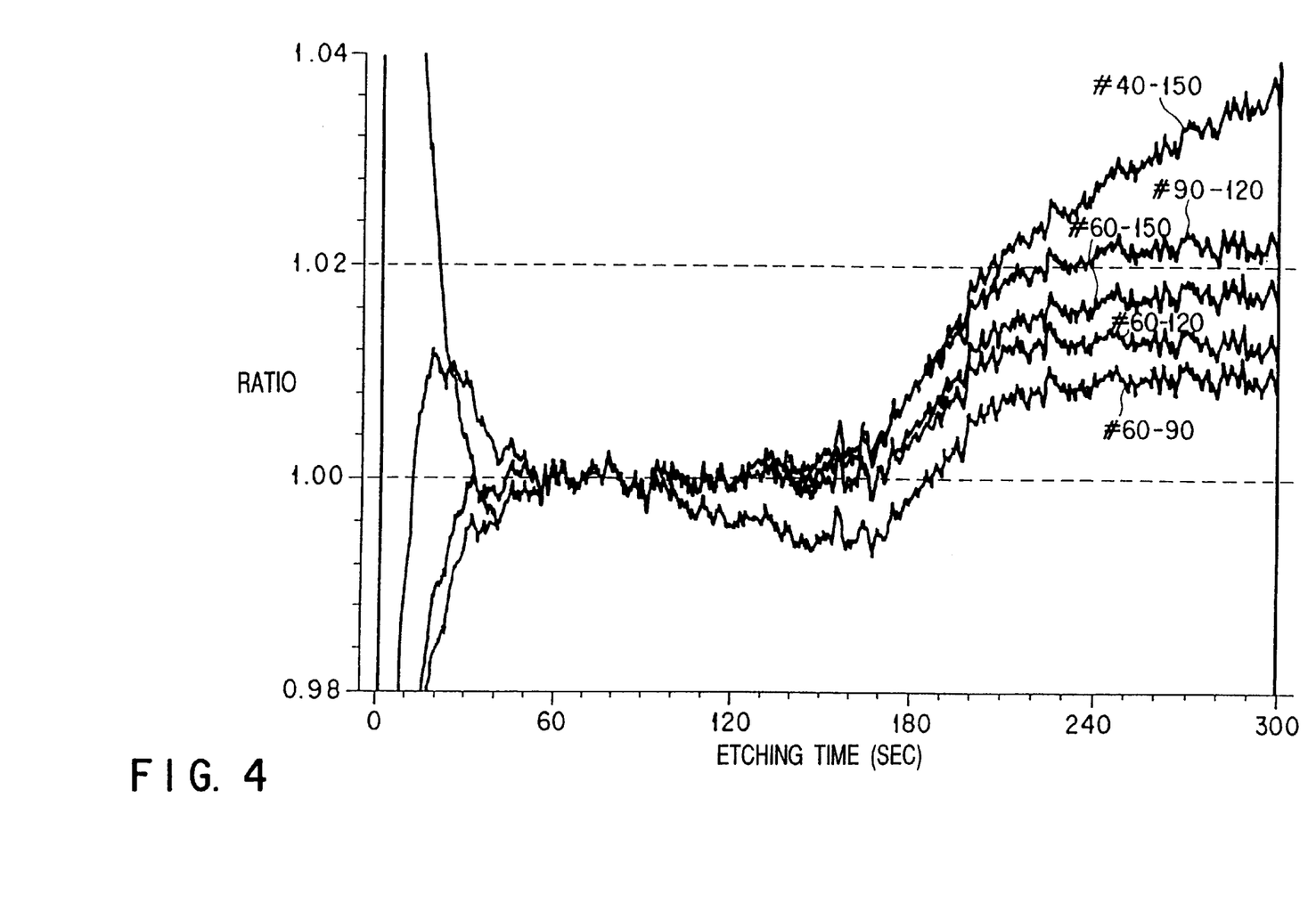
FIG. 4 is a graph showing the result of an experiment pertaining to the influence on end point detection by a difference in specified period.

The influence on end point detection by a difference in specified period was examined. In this experiment, the plasma etching process and detection of the emission intensity of the plasma were performed under completely the same conditions as those for the experiment described above, except that the specified period was changed.

FIG. 4 shows the result of the experiment pertaining to the influence on end point detection by the difference in the specified period. Referring to FIG. 4, curves #40-150, #90-120, #60-150, #60-120, and #60-90 are lines expressed by criterion {1} when the specified period is set to 40 sec to 150 sec, 90 sec to 120 sec, 60 sec to 150 sec, 60 sec to 120 sec, and 60 sec to 90 sec, respectively.

In the above embodiment, the end point of the etching process is determined by employing two types of gases, i.e., the etchant and the reaction product, as the observation targets. However, the present invention can also be employed when the combination of other two types of gases, i.e., an etchant and an etchant, or a reaction product and a reaction product, is employed as the observation targets. Also, when a signal indicating the opening degree of an APC (Auto Pressure Controller) or the position of the capacitor of a matching circuit is employed as one observation target in place of the emission intensity of the gas, and the intermediate expressions and the criterion expression described above are obtained, the end point of the etching process can be similarly detected.

An end point detection method according to another embodiment of the present invention, which is suitable when a fluctuation in characteristic curve as the observation target is small or when end point detection does not require high precision, will be described with reference to FIGS. 5 to 8. In these cases, end point detection can be performed without using the first and second deviations Da and Db described above, or by using only one observation target such as one type of gas.

A case wherein end point detection is performed without using the first and second deviations Da and Db described above will be described. When the method of this embodiment is compared with the method of the embodiment described above, although its detection precision decreases, signal processing by the controller becomes simple.

In this embodiment, prior to the start of the plasma process, i.e., the etching process, a specified period set before an ideal end point of the etching process is reached is determined, and is input and set in the controller, in the same manner as in the embodiment described above. Also, the first and second canonical expressions for obtaining first and second approximate expressions Fa(x) and Fb(x), which respectively approximate characteristic curves representing changes over time in emission intensities of two gases (e.g., process gas and product gas) employed as the observation targets, are determined, and are input and set in the controller. The determination period can be the same or different between the two observation target gases. The first and second canonical expressions can be the same or different functions.

Based on these preset conditions, the controller performs the following arithmetic process during the etching process, to determine the end point of the etching process.

First, the first and second approximate expressions Fa(x) and Fb(x) respectively approximating the characteristic curves representing the changes over time in emission intensities Ia and Ib of the two observation target gases in the plasma within the specified period, are obtained on the basis of the first and second canonical expressions.

When the specified period has elapsed, first and second intermediate expressions, e.g., Ia/Fa(x) and Ib/Fb(x), expressing the ratios of the emission intensities Ia and Ib of the two observation target gases in the plasma to the values of the first and second approximate expressions Fa(x) Fb(x), are obtained. Also, a criterion expression, e.g., [Ia/Fa(x)]/[Ib/Fb(x)], representing the ratio of the value of the first intermediate expression Ia/Fa(x) to that of the second intermediate expression Ib/Fb(x), is obtained.

On the basis of this criterion expression, the end point of the etching process is determined, and the dry etching apparatus is controlled to end the etching process.

The first and second intermediate expressions obtained after the lapse of the specified period can be expressions, e.g., Ia−Fa(x) and Ib—Fb(x), representing the differences between the emission intensities Ia and Ib and the values of the first and second approximate expressions Fa(x) and Fb(x). In this case, as the criterion expression, an expression representing the ratio of the value of the first intermediate expression to that of the second intermediate expression, e.g., [Ia−Fa(x)+M]/[Ib−Fb(x)+M], where M is an arbitrary constant, e.g., 1, is used. By adding M, the denominator can be prevented from becoming 0.

Figure 5:
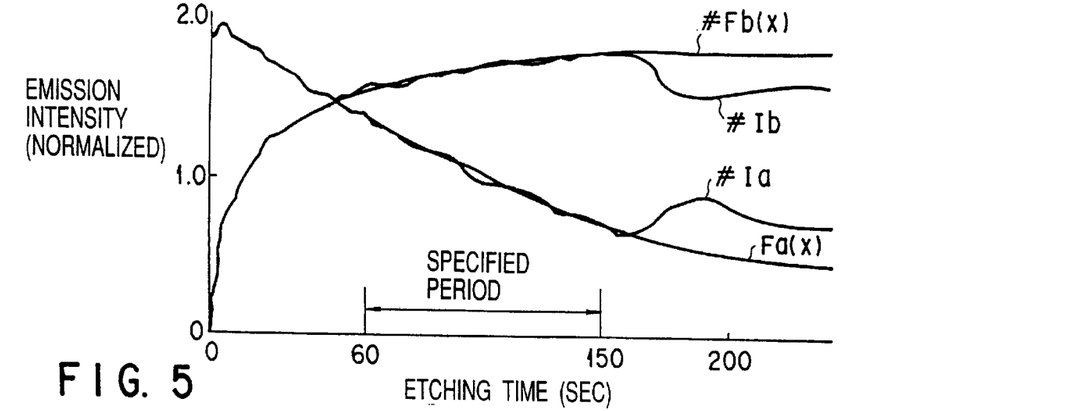
FIG. 5 is a graph showing changes over time in emission intensities of two observation target gases according to another embodiment of the present invention, and the models of the approximate curves of these changes over time.

FIG. 5 shows changes over time in emission intensities of the two observation target gases of this embodiment, and the model of their approximate curves.

Referring to FIG. 5, #Ia and #Ib denote characteristic curves representing the changes over time in emission intensities Ia and Ib of the two observation target gases throughout the entire period of the etching process. For example, the emission intensity Ia represents the characteristics of a gas generated by dissociation of the process gas supplied for the plasma process, and the emission intensity Ib represents the characteristics of a product gas generated by the plasma process. #Fa(x) and #Fb(x) denote approximate curves calculated in accordance with the first and second approximate expressions Fa(x) and Fb(x) respectively approximating the characteristic curves of the emission intensities within the specified period.

Figure 6:
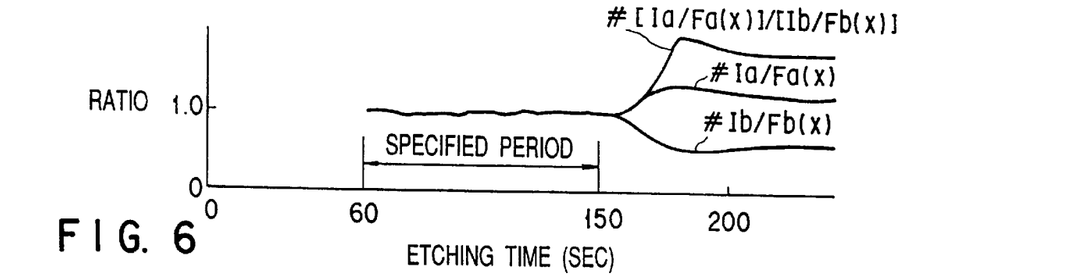
FIG. 6 is a graph showing curves expressed by intermediate expressions, a criterion expression, and the like of the embodiment described with reference to FIG. 5.

FIG. 6 shows curves expressed by the intermediate expressions, the criterion expression, and the like of this embodiment. Referring to FIG. 6, #Ia/Fa(x) and #Ib/Fb(x) respectively denote the curves of the first and second intermediate expressions Ia/Fa(x) and Ib/Fb(x). #[Ia/Fa(x)]/[Ib/Fb(x)] denotes the curve of the criterion expression of this embodiment. As shown in FIG. 6, in the curve #[Ia/Fa(x)]/[Ib/Fb(x)] of the criterion expression, a change near the end point of the etching process becomes larger than in the first and second intermediate expressions Ia/Fa(x) and Ib/Fb(x). Therefore, with this criterion expression, the end point of the etching process can be detected more easily.

A case wherein end point detection is performed by employing only one observation target such as one type of gas will be described. When the method of this embodiment is compared with the method of the embodiment described above, although the detection precision decreases, only one spectroscope is needed, and the signal processing of the controller is simplified.

In this embodiment, prior to the start of the plasma process, i.e., the etching process, a specified period set before an ideal end point of the etching process is reached is determined, and is input and set in the controller, in the same manner as in the embodiment described above. Also, a canonical expression for obtaining an approximate expression Fa(x), which approximates a characteristic curve representing a change over time in emission intensity of the gas employed as the observation target, is determined, and is input and set in the controller.

Based on these preset conditions, the controller performs the following arithmetic process during the etching process, to determine the end point of the etching process.

First, the approximate expression Fa(x), which approximates the characteristic curve representing the change over time in emission intensity Ia of the observation target gas in the plasma within the specified period, is obtained on the basis of the canonical expression.

When the specified period has elapsed, a criterion expression expressing the ratio or difference between the emission intensity Ia of the observation target gas in the plasma and the value of the approximate expression Fa(x) is obtained. For example, the criterion expression of this embodiment is expressed by Ia/Fa(x), Fa(x)/Ia, Ia−Fa(x), or Fa(x)−Ia.

On the basis of this criterion expression, the end point of the etching process is determined, and the dry etching apparatus is controlled to end the etching process.

Figure 7:
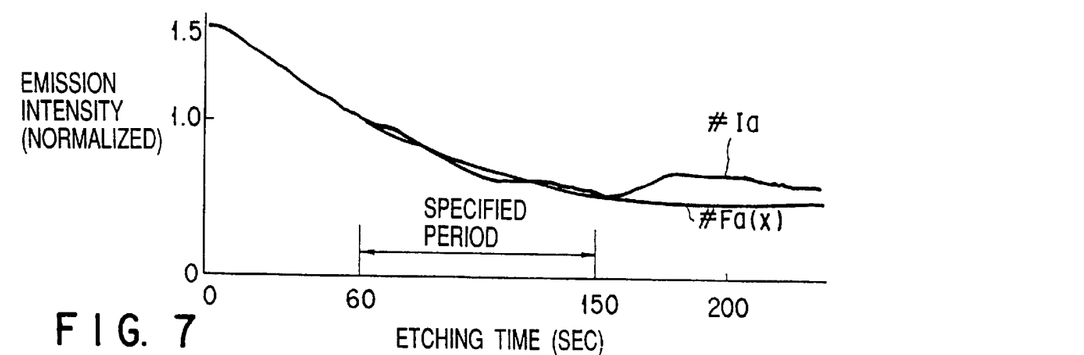
FIG. 7 is a graph showing a change over time of the emission intensity of an observation target gas according to still another embodiment of the present invention, and the model of the approximate curve of this change over time.

FIG. 7 shows a change over time in emission intensity of the observation target gas of this embodiment, and the model of its approximate curve. Referring to FIG. 7, #Ia denotes a characteristic curve representing the change over time in emission intensity Ia of the observation target gas throughout the entire period of the etching process. #Fa(x) denotes an approximate curve calculated in accordance with the approximate expression Fa(x) approximating the characteristic curve of the emission intensity within the specified period.

Figure 8:
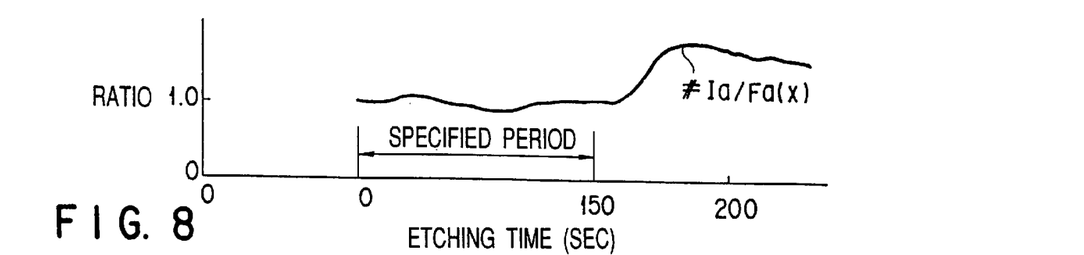
FIG. 8 is a graph showing a curve expressed by a criterion expression of the embodiment described with reference to FIG. 7.

FIG. 8 shows a curve #Ia/Fa(x) expressed by the criterion expression of this embodiment. As shown in FIG. 8, in the curve #Ia/Fa(x) of the criterion expression, a change near the end point of the etching process becomes larger than in the curve of the emission intensity Ia. Therefore, with this criterion expression, the end point of the etching process can be detected more easily.

In the two embodiments described with reference to FIGS. 5 to 8, the end point of the etching process can be determined with reference to, e.g., a time point at which the average gradient of the curve expressed by the criterion expression changes largely. Alternatively, the end point of the etching process can be determined with reference to a time point at which the absolute value of the calculation value of the criterion expression becomes equal to the threshold value or more. In either case, a time point at which a predetermined time for over-etching, which is obtained through experiences, has elapsed since the reference time point can be determined as the end point of the etching process.

The three embodiments described above describe an etching apparatus for etching a wafer W. The present invention can also be applied to various types of plasma processing apparatuses such as an ashing apparatus. In place of the wafer W, for example, an LCD glass substrate can be used as the target object.

More specifically, the present invention is not limited by the embodiments described above, and can be practiced in various embodiments without departing from the spirit and scope of the invention. For example, in the criterion expression for determining the end point of the etching process, one of parameters such as the emission intensities, the approximate expressions, the intermediate expressions, and the like, which is to be set as the denominator or numerator, is not limited by the examples described above, but can be arbitrarily changed within the spirit and scope of the present invention.

What is claimed is:

1. An end point detection method in a semiconductor plasma process, comprising the steps of:
   determining first and second specified periods set before an ideal end point of the plasma process is reached;
   subjecting a target object to the plasma process;

obtaining, during the plasma process, a first approximate expression which approximates a characteristic curve representing a change over time in emission intensity of a first gas in the plasma within the first specified period, and a second approximate expression which approximates a characteristic curve representing a change over time in emission intensity of a second gas in the plasma within the second specified period;

obtaining, during the plasma process, first and second intermediate expressions representing ratios or differences between the emission intensities of the first and second gases in the plasma and values of the first and second approximate expressions after the first and second specified periods elapse;

obtaining a criterion expression representing a ratio of the first intermediate expression to the second intermediate expression; and determining an end point of the plasma process on the basis of the criterion expression.

2. The method according to claim 1, wherein the first and second approximate expressions are obtained by using different functions.

3. The method according to claim 1, wherein the first and second specified periods are the same period.

4. The method according to claim 1, wherein one of the first and second gases is a gas generated by dissociation of a process gas supplied for the plasma process, and the other one is a product gas generated by the plasma process.

5. The method according to claim 1, wherein a time point at which an average gradient of a curve expressed by the criterion expression changes largely is determined as a reference for determining the end point.

6. The method according to claim 1, wherein a time point at which an absolute value of a calculation value of the criterion expression becomes not less than a threshold value is determined as a reference for determining the end point.

7. An end point detection method in a semiconductor plasma process, comprising the steps of:

determining first to fourth specified periods set before an ideal end point of the plasma process is reached;

subjecting a target object to the plasma process;

obtaining, during the plasma process, a first approximate expression which approximates a characteristic curve representing a change over time in emission intensity of a first gas in the plasma within the first specified period, and a second approximate expression which approximates a characteristic curve representing a change over time in emission intensity of a second gas in the plasma within the second specified period;

obtaining, during the plasma process, a first deviation corresponding to a deviation of the emission intensity of the first gas in the plasma with respect to a value of the first approximate expression within the third specified period, and a second deviation corresponding to a deviation of the emission intensity of the second gas in the plasma with respect to a value of the second approximate expression within the fourth specified period;

obtaining, during the plasma process, first and second intermediate expressions representing ratios or differences between the emission intensities of the first and second gases in the plasma and the values of the first and second approximate expressions after the first to fourth specified periods elapse;

correcting the first and second intermediate expressions with the first and second deviations, and obtaining a criterion expression representing a ratio of the first intermediate expression to the second intermediate expression; and determining an end point of the plasma process on the basis of the criterion expression.

8. The method according to claim 7, wherein the criterion expression is a ratio, weight-corrected with a correction coefficient, of the first intermediate expression to the second intermediate expression, and the correction coefficient is a ratio of the first deviation to the second deviation.

9. The method according to claim 8, wherein when the first and second approximate expressions are respectively $Fa(x)$ and $Fb(x)$, the emission intensities of the first and second gases in the plasma are respectively $Ia$ and $Ib$, and the correction coefficient is $\alpha$, the first and second intermediate expressions are respectively $Ia/Fa(x)$ and $Ib/Fb(x)$, and the criterion expression is expressed by a ratio of $[Ia/Fa(x)]$ to $\{\alpha[Ib/Fb(x)-1]+1\}$.

10. The method according to claim 8, wherein when the first and second approximate expressions are respectively $Fa(x)$ and $Fb(x)$, the emission intensities of the first and second gases in the plasma are respectively $Ia$ and $Ib$, and the correction coefficient is $\alpha$, the first and second intermediate expressions are respectively $Ia-Fa(x)$ and $Ib-Fb(x)$, and the criterion expression is expressed by a ratio of $[Ia-Fa(x)+M]$ to $\{\alpha[Ib-Fb(x)]+M\}$ where $M$ is an arbitrary constant.

11. The method according to claim 7, wherein the first and second approximate expressions are obtained by using different functions.

12. The method according to claim 7, wherein the first and second deviations are respectively standard deviations.

13. The method according to claim 7, wherein the first and second deviations are differences between the maximum and minimum values of deviations.

14. The method according to claim 7, wherein the first to fourth specified periods are the same period.

15. The method according to claim 7, wherein one of the first and second gases is a gas generated by dissociation of a process gas supplied for the plasma process, and the other one is a product gas generated by the plasma process.

16. The method according to claim 7, wherein a time point at which an average gradient of a curve expressed by the criterion expression changes largely is determined as a reference for determining the end point.

17. The method according to claim 7, wherein a time point at which an absolute value of a calculation value of the criterion expression becomes not less than a threshold value is determined as a reference for determining the end point.

* * * * *

UNITED STATES PATENT AND TRADEMARK OFFICE
CERTIFICATE OF CORRECTION

PATENT NO.    : 6,297,064 B1
DATED         : October 2, 2001
INVENTOR(S)   : Koshimizu It is certified that error appears in the above-identified patent and that said Letters Patent is hereby corrected as shown below:

Title page,
Item [73], Assignees information should read:

-- [73]   Assignees: Tokyo Electron AT Limited, Miyagi-gun;
                    Japan Science and Technology Corporation,
                    Kawaguchi-shi, both of (JP) --

Signed and Sealed this

First Day of January, 2002

Attest:

JAMES E. ROGAN
*Attesting Officer*    *Director of the United States Patent and Trademark Office*